United States Patent
Itoi (10) Patent No.: US 6,383,141 B1
(45) Date of Patent: May 7, 2002

(54) ULTRASOUND TRANSDUCER

(75) Inventor: Hiromu Itoi, Omiya (JP)

(73) Assignee: Fuji Photo Optical Co., Ltd., Omiya (JP)

( * ) Notice: Subject to any disclaimer, the term of this patent is extended or adjusted under 35 U.S.C. 154(b) by 0 days.

(21) Appl. No.: 09/518,091

(22) Filed: Mar. 3, 2000

(30) Foreign Application Priority Data

Mar. 4, 1999 (JP) .............................. 11-056908

(51) Int. Cl.[7] .................................. A61B 8/12
(52) U.S. Cl. ...................................... 600/459
(58) Field of Search .................. 600/437, 459, 600/443, 455, 463; 310/324, 328, 330, 334; 29/25.35; 73/620–632

(56) References Cited

U.S. PATENT DOCUMENTS 4,398,116 A * 8/1983 Lewis ......................... 310/334
5,320,104 A * 6/1994 Fearnside et al. ............ 600/463
5,377,166 A * 12/1994 Kuhn ............................ 367/135

* cited by examiner

Primary Examiner—Marvin M. Lateef
Assistant Examiner—Ali M. Imam
(74) Attorney, Agent, or Firm—Oblon, Spivak, McClelland, Maier & Neustadt, P.C.

(57) ABSTRACT

An ultrasound transducer having transducer elements arrayed in a polygonal shape on a common plane. The polygonal array of transducer elements includes a core unit consisting of a single transducer element of a polygonal shape and a plural number of frame units each consisting of a plural number of transducer elements arranged in a polygonal shape around the transducer element of the core unit. Each one of the transducer elements of the frame units are formed in the shape of a square block and electrically connected to adjacent transducer elements of the same frame unit but insulated from transducer elements of an adjacent frame unit through an insulating coat layer.

12 Claims, 8 Drawing Sheets

ULTRASOUND TRANSDUCER

BACKGROUND OF THE INVENTION

1. Field of the Art

This invention relates to an ultrasound transducer with an electronic focusing function.

2. Prior Art

Medical ultrasound examination systems are used mainly for acquiring information on conditions of patient's body tissues or the like. Ultrasound examination systems are equipped with an ultrasound probe including an ultrasound transducer consisting of a piezoelectric transducer element or elements. The transducer element of this sort functions to transmit an ultrasound beam into a patient's body and to receive echo signals from body tissues in various portions of a tomographic area or in positions of different acoustic impedances. The received return echo signals received by the transducer element are converted into electric signals, which are then transferred to an ultrasound sound signal processor to undergo various signal processing operations and thereby converted into video signals to be displayed on a viewing screen as ultrasound images. An ultrasound image is displayed by way of variations in luminosity on a large number of acoustic lines which are set on a viewing screen according to distances of scanned portions as converted from time durations to reception of return echo signals. The traveling or transmission speed of ultrasound waves in human body is almost same as transmission speed in water.

In order to improve the quality of ultrasound images, it is necessary to enhance the intensity of return echo signals. Further, for the purpose of increasing the range of penetration into patient's body by an ultrasound beam, it is desirable that the output power of an ultrasound beam should be as large as possible. The ultrasound beam power is determined depending upon the active surface area of an ultrasound transducer. Namely, in order to obtain an ultrasound beam of higher output power, it becomes necessary to employ an ultrasound transducer with a broader active surface area. Generally, an ultrasound beam which is transmitted from a transducer element tends to spread or diverge in the travel direction, and, particularly in case of a transducer with a broad active surface, this tendency becomes very conspicuous to invite degradations in directional resolution. Besides, in receiving return echoes from various tomographic scan areas of different acoustic impedances, delays in signal reception time occurs in peripheral portions of the active surface as compared with center portions thereof. That is to say, delays in signal reception time phase constantly occur to an ultrasound transducer to increase the width of received pulse signals to a corresponding degree. These delays in reception time phase result in degradations in picture quality and sharpness of ultrasound images to be produced.

In this regard, it has been known and attempts have been made to provide an ultrasound transducer with an acoustic focusing function. Typical of the attempts in this particular aspect is the provision of an acoustic lens on the surface of an ultrasound transducer. Nevertheless, acoustic lenses are normally fixed in focal distance and therefore incapable of focusing to a position which is at a desired depth or of shifting a focus position over a certain range in depth in the manner as in the so-called dynamic focusing.

Ultrasound scan systems are generally categorized into a mechanical scan type and an electronic scan type. An electronic scan type ultrasound transducer unit is constituted by a large number of transducer elements which are arrayed in a predetermined direction. The arrayed transducer elements are sequentially driven in a certain timing to scan a predetermined range. The width of a transmitted ultrasound beam can be narrowed to a certain extent by controlling the timing in driving the respective transducer elements of the ultrasound transducer unit. This is the so-called electronic focusing. It is also possible to apply the electronic focusing to return echo signals. Namely, a delay circuit can be connected to each one of the transducer elements to adjust the delay time in signal reception independently of each other. In this case, the respective transducer elements can be operated in phase with each other in signal reception time by setting the delay time of each transducer element at an appropriate value according a difference in distance from a focus position to correct a delay in signal reception time.

In applying the above-mentioned electronic focusing, it is desirable to converge an ultrasound beam to a circular shape in section and to a minimal diameter and at the same time to bring the respective transducer elements exactly in phase with each other in signal reception time. For this purpose, a plural number of transducer elements of an ultrasound transducer unit are arranged in an annular array and in such concentric relations as to have different signal receiving positions from each other.

Regarding the piezoelectric material for the ultrasound transducer elements, it is the general practice to employ ceramic semiconductor such as titanium zirconate, barium titanate or the like. The ceramic semiconductor materials as just mentioned have a drawback that it is difficult to fabricate the transducer elements into a desired shape. However, it is necessary to form transducer elements into annular or arcuate shapes especially in case they are to be arranged in an annular array, despite the difficulties which are encountered in machining the ceramic semiconductor material precisely to predetermined surface curvatures. Due to high probabilities of fractures and cracking in a fabrication process, transducer elements of this sort are usually very expensive. Lately, in addition to the ceramic semiconductor materials as mentioned above, high polymer piezoelectric materials have been developed and put in use. Examples of the high polymer piezoelectric materials include PVDF (polyvinylidene fluoride), copolymer of VF (vinyl fluoride) and TrFE (trifluoroethylene) or TFE (tetrafluoroethylene), alternating copolymer P (VCDN/VAc) of VCDN (vinylidene cyanide) and Vac (vinyl acetate) and the like. The use of such a high polymer piezoelectric material may make it possible to arrange electrodes on piezoelectric elements substantially annularly and in such a way as to produce the same effects as an annular array without necessitating to machine the respective piezoelectric elements into an annular or arcuate shape. Nevertheless, as compared with the ceramic semiconductor type transducer elements, generally transducer elements of a high polymer type piezoelectric material are inferior in transmission efficiency and mechanical strength.

SUMMARY OF THE INVENTION

In view of the foregoing situations, it is an object of the present invention to provide an ultrasound transducer which can be fabricated in an advantageously facilitated manner and which is capable of electronically focusing an ultrasound beam to a desired position and satisfactory in signal transmission/reception efficiency.

It is another object of the present invention to provide an ultrasound transducer employing a polygonal array of transducer elements which are satisfactory in mechanical strength and can produce electronic focusing effects akin to an annular array.

It is still another object of the present invention to provide an ultrasound transducer having transducer elements of straight block-like forms arranged in a polygonal array which can operate substantially in the same manner as an annular array.

In accordance with the present invention, the above-stated objectives are achieved by the provision of an ultrasound transducer which basically comprises: an array of transducer elements arranged in a polygonal shape on a common plane, the array of transducer elements including a core unit consisting of a single transducer element of a polygonal shape and a plural number of frame units each consisting of a plural number of transducer elements arranged in a polygonal shape around the transducer element of the core unit, each one of the transducer elements of the frame units being formed in the shape of a straight square block and being electrically connected to adjacent transducer elements of the same frame unit but insulated from transducer elements of an adjacent frame unit through an insulating coat layer.

In this instance, preferably each one of the transducer elements of the core and frame units is constituted by a ceramic semiconductor type piezoelectric material which is superior in signal transmission efficiency and mechanical strength. Besides, the transducer elements of the core and frame units are so dimensioned as to have substantially the same active surface area.

The polygonal array does not have the respective transducer elements arranged on concentric circles. However, the transducer elements of the frame units are arranged to form closed polygonal loops around the transducer element of the core unit in the fashion of a pseudo annular array. The polygonal array approaches a circle in shape if the number of apexes is increased from tetragon to hexagon, from hexagon to octagon and so forth, but an increased number of apexes will make it more complicate to fabricate and assemble the transducer elements of the respective frame units. Accordingly, it is most preferable to arrange the frame units in an square or hexagonal array in view of closeness to an annular array in shape as a whole and easy fabrication and assembling of transducer elements. The transducer elements of the respective frame units can be fabricated easily in a facilitated manner because they are in the form of straight square blocks without any curved surfaces.

Each one of the transducer elements of the core and frame units should have an electrode on front and back sides thereof. The back side of each transducer elements can be connected to a common electrode. Accordingly, in arraying the respective transducer elements in a polygonal shape, the back side of each transducer element is placed on a common electrode sheet. On the other hand, a front electrode is laminated on the front side of each one of the transducer elements of the core and frame units.

The front electrodes on the front sides of the transducer elements of each frame unit should be connected with front electrodes of adjoining transducer elements. Namely, the respective transducer elements of the same frame unit are electrically connected with each other through conductive members, but should be insulated from transducer elements of an adjoining inner or outer frame unit. For this purpose, for instance, it is possible to provide an air gap or to interpose a sheet-like insulating member between transducer elements of inner and outer frame units. In this regard, from the standpoint of facilitating assembling work, it is preferable to provide insulating coat layers at least on opposing side surfaces of transducer elements of adjoining inner and outer frame units which face toward each other, permitting to locate the transducer elements of the two adjoining frame units closely to each other. For the necessity of drawing wires to the back side of the transducer elements of the core unit and the frame units, except the transducer elements of an outermost frame unit, through holes are normally required. However, for this purpose, it is advantageous to provide a notched portion at one corner of a transducer element in each frame unit. A notched portion of this sort can substantially serve as a through hole and provides a passage for drawing a wire from front electrodes of the transducer elements of each frame unit to the back side of the transducer.

The above and other objects, features and advantages of the present invention will become apparent from the following particular description, taken in conjunction with the accompanying drawings which show by way of example some preferred embodiments of the invention.

DESCRIPTION OF PREFERRED EMBODIMENTS

Figure 1:
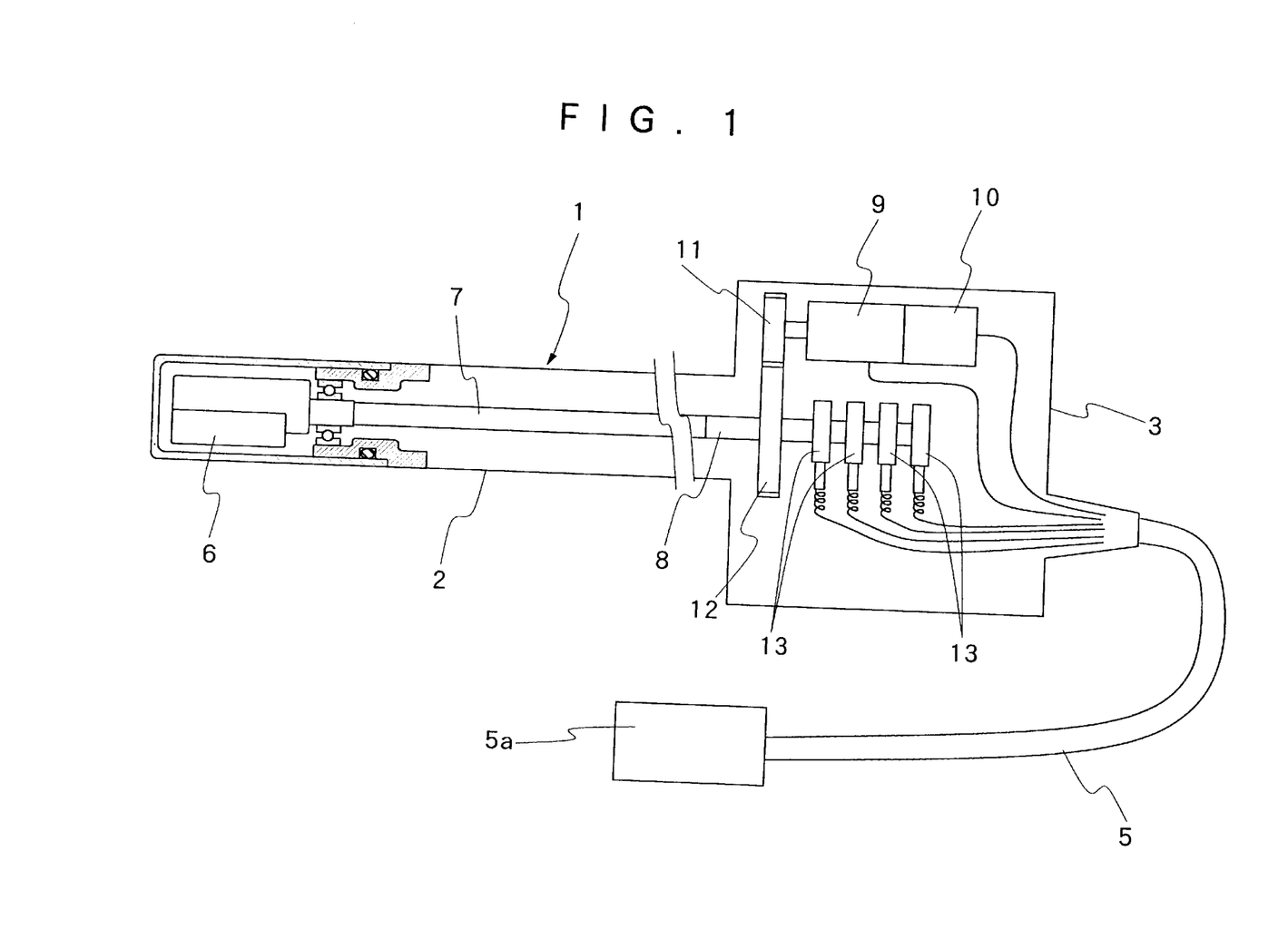
FIG. 1 is a schematic view of an ultrasound probe for an ultrasound examination system.

Hereafter, the present invention is described more particularly by way of its preferred embodiments with reference to the accompanying drawings. Schematically shown in FIG. 1 is the general layout of an ultrasound examination system having an ultrasound probe 1. The ultrasound probe 1 is provided with a manipulating control head 3 at a proximal end of an insert portion 2 to be introduced into a body cavity of a subject. Connected to the manipulating control head 3 is a cable 5 which is provided with a connector 5a at its proximal end to be disconnectibly connected to an ultrasound image processing and observing terminal 4 (FIG. 2).

Accommodated within a cap 2a, which is provided at the fore distal end of the insert portion 2, is an ultrasound transducer 6 to scan body tissues of a subject from an intracavitary site of interest. This ultrasound transducer 6 is of a radial scan type and therefore rotatable within the cap 2a. In addition to radial scans, for example, it is possible to make linear or convex scans by the use of ultrasound transducer 6. The ultrasound transducer 6 can be put in rotation by remote control. For this purpose, the ultrasound transducer 6 is connected to a fore end of a flexible rotation transmission shaft 7. The flexible rotation transmission shaft 7 is constituted, for example, by a tightly wound coil tube or the like, and a signal cable which is connected to the ultrasound transducer 6 is passed through the coil tube of the rotation transmission shaft 7. The other proximal end of the flexible transmission shaft 7 is extended into the manipulating control head 3 and coupled with a rotational shaft 8. Provided within the manipulating control head 3 are a rotational drive motor 9 and an encoder 10. A drive gear 11 which is mounted on an output shaft of the motor 9 is meshed with a follower gear 12 which is mounted on the rotational shaft 8. Further, the cable which is passed through the flexible rotation transmission shaft 7 is connected to the afore-mentioned cable 5 through a slip-ring type or other rotary connector 13 which is mounted on the rotational shaft 8.

Upon actuating the motor 9, the rotational shaft 8 is driven into rotation to rotate the flexible rotation transmission shaft 7 about the axis thereof, and as a result the ultrasound transducer 6 is put in rotation. The rotational angle of the ultrasound transducer 6 is detected by the encoder 10. At the time of an ultrasound scan, according to signals from the encoder 10, the ultrasound transducer 6 is driven to transmit ultrasound pulse signals into the body of a subject at predetermined angular intervals of its rotation, while receiving return echo signals from the subject. The return echo signals which are converted into electric signals by the transducer 6 are transferred to the ultrasound image processing and observing terminal 4.

Figure 2:
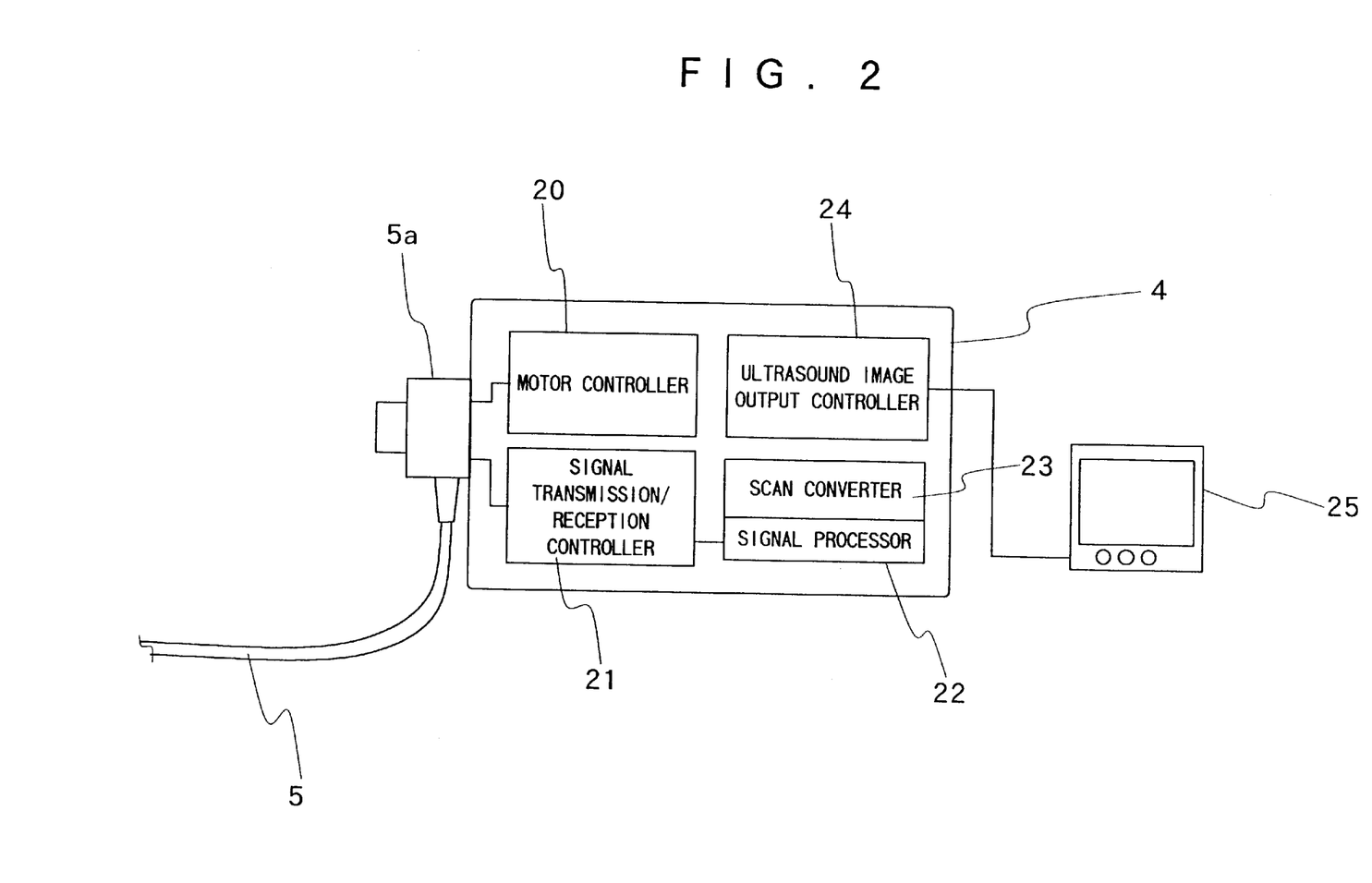
FIG. 2 is a diagrammatic illustration of an ultrasound image processing and observing terminal.

As illustrated in FIG. 2, the ultrasound image processing and observing terminal 4 includes a motor controller 20 which controls the operation of the motor 9, a signal transmission/reception controller 21, a signal processor 22, a scan converter 23 and an ultrasound image output controller 24. The motor controller 20 which controls the rotation of the ultrasound transducer 6 includes a switch (not shown) which is provided on the manipulating control head 3 thereby to permit an operator to start and stop rotation of the ultrasound transducer 6. The signal transmission/reception controller 21 is adapted to apply a drive signal to the ultrasound transducer for transmission of an ultrasound pulse signal at predetermined angular intervals, on the basis of angular position signals which are received from the encoder 10. This is a signal transmission mode of the ultrasound probe. After transmission of an ultrasound pulse signal, the operation of the probe is switched to a signal reception mode to receive return echoes from the subject on the transducer 6. The operation of the probe is alternately switched to the transmission mode and the reception mode by the signal transmission/reception controller 21. The received return echo signals are fed to the signal processor 22 which performs predetermined signal processing operations including amplification and wave detection in the manner well known in the art. Signals from the signal processor 22 are fed to the scan converter 23, along with angular position signals from the encoder 10, and thereby processed to produce video signals to be displayed as ultrasound images. The resulting video signals are stored in a frame memory of the scan converter 23. As soon as a frame of video signals are stored in the frame memory, these video signals are read out and output to the monitor 25 under control of the scan converter 23.

Figure 3:
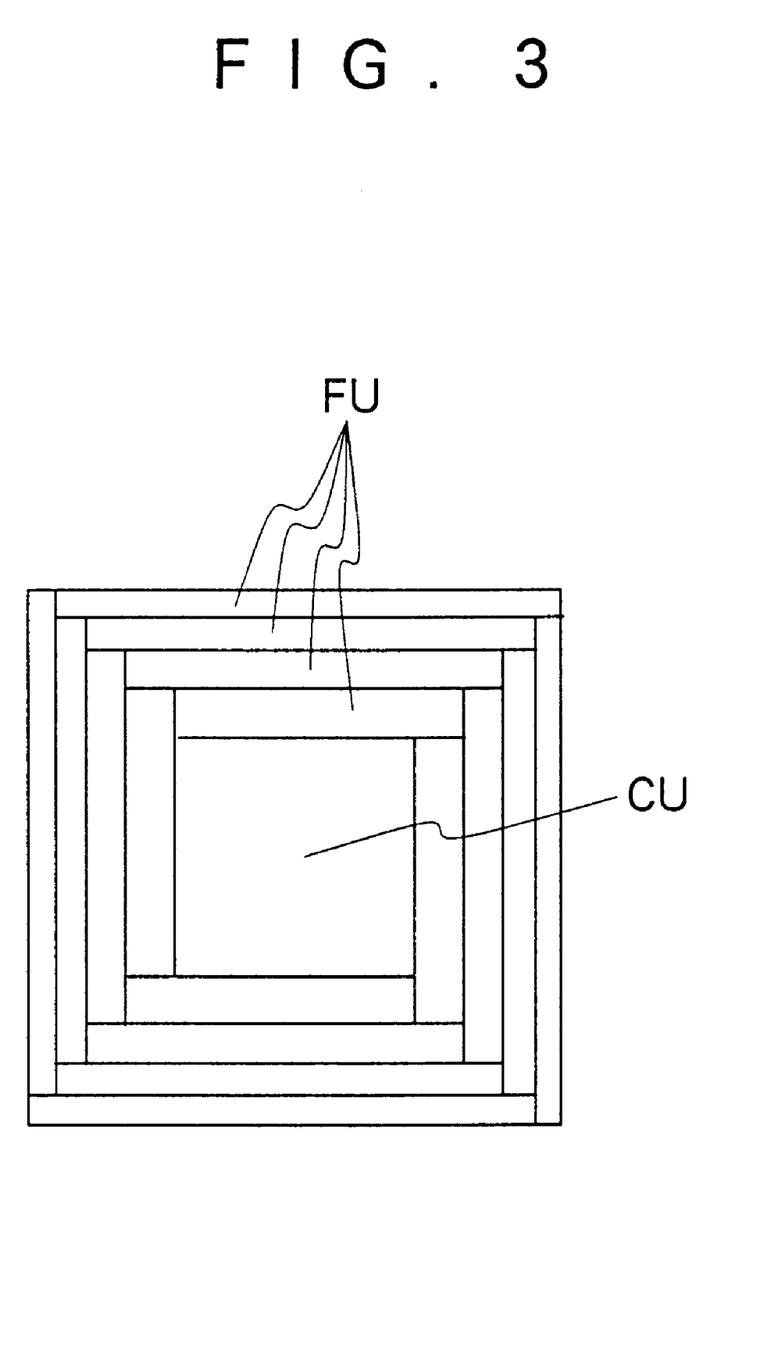
FIG. 3 is a schematic view of an ultrasound transducer.

In the ultrasound examination system which is arranged as described above, the ultrasound transducer 6 which is provided at the fore distal end of the insert portion 2 of the ultrasound probe 1 is arranged to have an electronic focusing function. For instance, as shown schematically in FIG. 3, the ultrasound transducer 6 as a whole is generally formed in a square shape. The ultrasound transducer 6 is constituted by a large number of transducer elements in the form of a core unit CU which is located in a center position, and a plural number of frame units FU which are arranged to form rectangular parallel frames around the core unit CU. The frame units FU which contribute to the electronic focusing function. It follows that the greater the number of frame units, the higher becomes the electronic focusing capability of the transducer. In the particular embodiment shown, each frame unit FU is constituted by four transducer elements, preferably of the ceramic semiconductor type which has satisfactory transmission characteristics. All of the transducer elements in the frame units CU and FU have substantially the same surface area. Therefore, the transducer elements in an inner frame unit FU are greater in width and smaller in length, while the transducer elements in an outer frame unit FU are smaller in width and larger in length.

Figure 4:
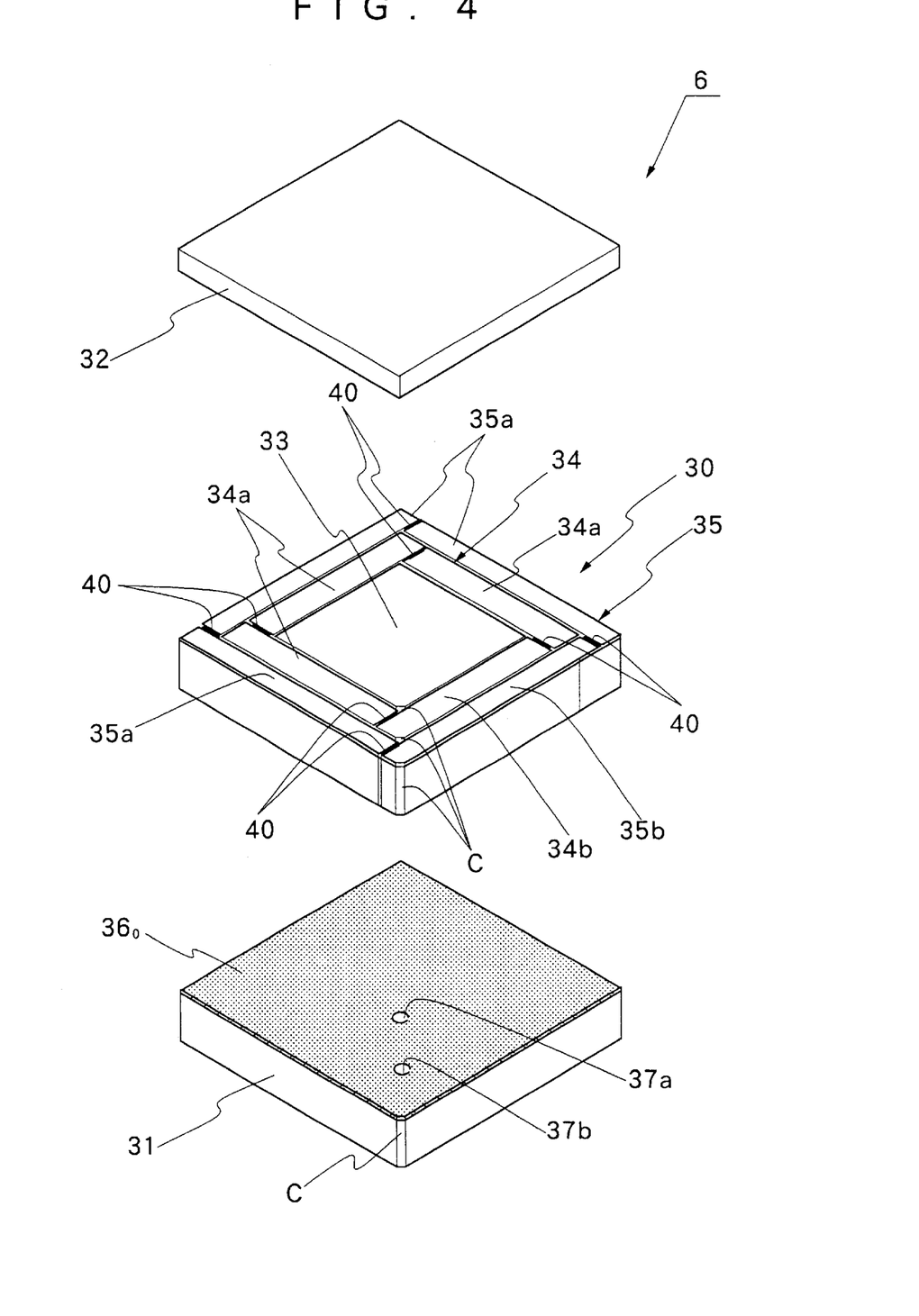
FIG. 4 is an exploded view of an ultrasound transducer embodying the present invention.
Figure 5:
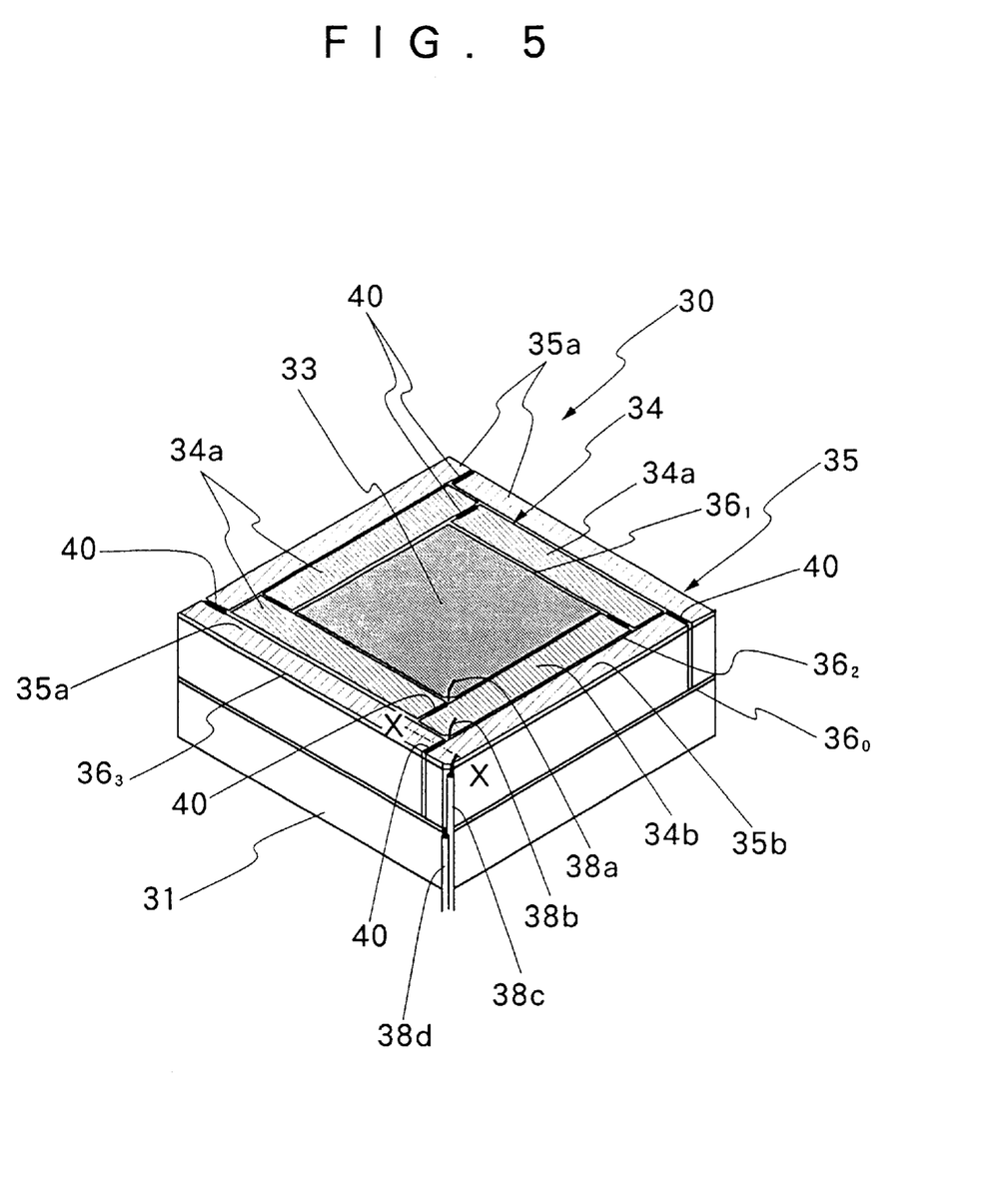
FIG. 5 is a schematic outer view of the ultrasound transducer of FIG. 4, showing transducer elements and packing material in an assembled state.

Schematically shown in FIGS. 4 and 5 is the construction of the ultrasound transducer 6. The ultrasound transducer 6 is largely constituted by an transducer element assembly 30 which is sandwiched between backing material 31 of a predetermined thickness and an acoustic matching layer 32 which is laminated on an active signal transmission/reception surface of the transducer. If necessary, an acoustic lens is bonded on the acoustic matching layer 32. A core unit 33, consisting of a single transducer element, is located centrally of the transducer element assembly 30, and a first frame unit 34, formed by four transducer elements, is located on the outer side of the core unit 33 in such a way as to circumvent the latter. A second frame unit 35 which is similarly formed of four transducer elements is located on the outer side of the above-mentioned first frame unit 34 in such a way as to circumvent the latter. Although two frame units are shown in these figures for the sake of simplification of illustration, it is desirable to provide third and fourth or more frame units successively on the outer side of the second frame unit 35 for the purpose of enhancing the electronic focusing function.

In this instance, the transducer elements in the first and second frame units 34 and 35 differs from each other in length and width. However, the three transducer elements 34a of the first frame unit 34 as well as the three transducer elements 35a of the second frame unit 35 are identical with each other in shape and dimensions. The remaining transducer elements 34b and 35b of the first and second frame units 34 and 35 are also same as other elements of the unit in shape except that one corner portion is chamfered or notched as seen in the drawings. Thus, both of the frame units 34 and 35 are similarly constituted by transducer elements in the form of straight square blocks which differ from each other simply in width and length.

Figure 6:
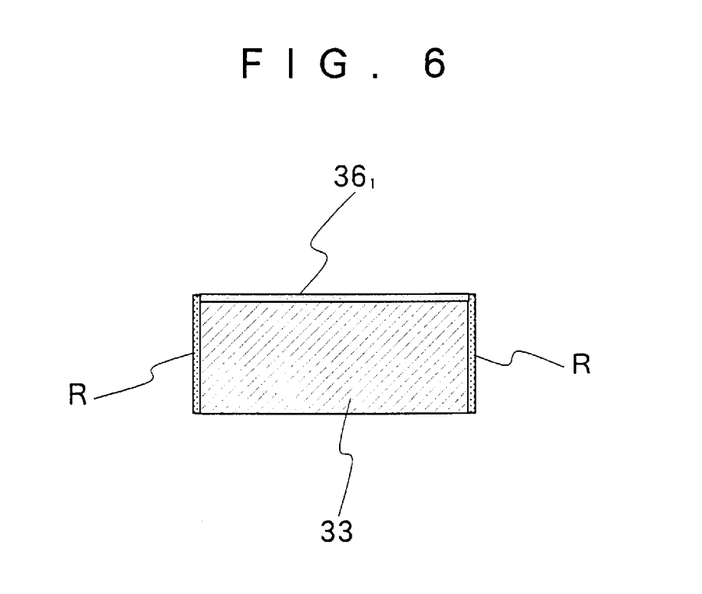
FIG. 6 is a schematic sectional view of a core transducer element.
Figure 7:
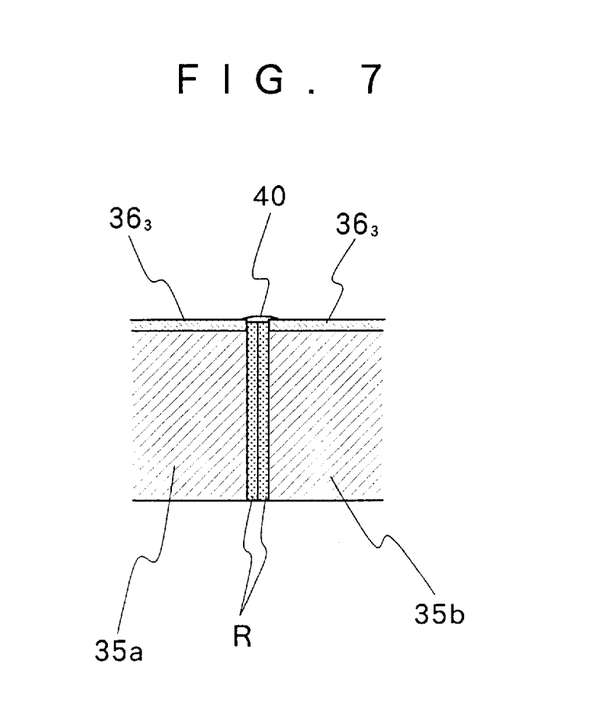
FIG. 7 is a fragmentary sectional view taken on line X—X of FIG. 5.

Shown in FIGS. 6 and 7 are the sole transducer element of the core unit 33 and two adjacent transducer elements 34a and 34b of the first frame unit, respectively. The transducer elements 35a and 35b of the outermost frame unit 35 are omitted in these figures because they are identical with the transducer elements 34a and 34b except the differences in width and length. The core transducer element 33 formed in a predetermined thickness and substantially in a square shape in plan view, and provided with a vertically notched portion C at one corner thereof. As seen in FIG. 6, the core transducer element 33 is laminated with a thin-film electrode $36_1$, on its front surface, and provided with insulating coat layers R on four lateral sides. The piezoelectric material is exposed on the back side of the transducer element. As clear from FIG. 7, the transducer elements 35a and 35b of the second frame unit 35 basically have the same construction as the core transducer element 33 in section (the same applies to the transducer elements 34a and 34b of the first frame unit 34). More specifically, the transducer elements 35a and 35b are laminated with a thin-film electrode $36_3$ on the respective front surfaces, and provided with insulating coat layers R on four lateral sides thereof. Piezoelectric material is exposed on the back side away from the thin-film electrode $36_3$. Further, the transducer elements 34a and 34b of the first frame unit 34 are constructed in a similar manner and are each provided with an electrode $36_2$.

As described above, the transducer element 33 of the core unit and the transducer elements 34 and 35 of the first and second frame units are formed with front electrodes $36_1$, $36_2$ and $36_3$ on the front side, respectively, while a common electrode is provided on the back side of the transducer. More specifically, as shown in FIG. 6, a sheet-like back electrode $36_0$ is laminated on the front side of the backing material 31. Further, as shown in FIG. 4, a through hole 37 is bored through the backing material 31 and the laminated back electrode $36_0$ at a number of positions (at two positions 37a and 37b in the case of the particular embodiment shown). These through holes are used for passing wires from the respective front electrodes 361 and 362 of the transducer elements of the core unit 33 and the frame unit 34, except at least the wires from the transducer elements of the outermost second frame unit 35.

The ultrasound transducer unit assembly 30 can be formed, for example, by assembling transducer elements of the core unit 33 and the frame units 34 and 35 in the manner as follows. Firstly, an adhesive is applied on the surface of the back electrode $36_0$ which is laminated on the backing material 31, and nextly the transducer element 33 of the core unit is fixedly bonded in a center position on the back electrode $36_0$. Then, wire 38 is connected to the front electrode $36_1$, of the core transducer element 33. The wire 38 from the front electrode $36_1$, is extended downward along the notched corner portion C and led out on the lower side by way of a through hole 37a in the backing material 31.

In the next place, the three transducer elements 34a and one notched transducer element 34b of the first frame unit 34 are located and fixed in position in such a way as to form a frame structure which circumvents the core transducer element 33. Since insulating coat layers R are formed on the lateral sides of the core transducer element 33 as well as on the lateral sides of the transducer elements 34a and 34b, these transducer elements can be positioned in contact with each other. Accordingly, adjoining surfaces of butt-joined transducer elements and the core transducer element are fixedly bonded to each other by the use of an adhesive. The adhesive agent to be used for this purpose should be an electrically insulating type. Wire 39 which is connected to the front electrode $36_2$ is passed through and extended downward along the notched portion C of the transducer element 34b. Further, the wire 39 is extended to the back side of the backing material 31 by way of a through hole which is provided in a corresponding position. In this state, however, the three transducer elements 34a are not electrically connected with the front electrode $36_2$ of the transducer element 34b. Therefore, a conductive member 40 is interposed between adjacent front electrodes $36_2$ to electrically connect same with each other.

In a similar manner, the transducer elements 34 and 35 of the second frame unit are assembled together, and wire 41 is connected to the front electrode 263. The wire 41 for the transducer elements 35 of the outermost frame unit is extended downward along the notched portion C at one corner of the transducer element 35b and further downward along a notched portion C which is similarly provided at one corner of the backing material 31.

In this instance, in electrically connecting adjacent transducer elements of a frame unit with each other by means of the conductive member 40, it is possible to deposit conductive solder or paste of silver or the like or to put thereon a thin-film conductive member such as a copper foil or the like. In this regard, the transducer elements of the same frame unit should be electrically connected with each other but should be insulated from the core transducer element and transducer element of other frame unit, in a secure and reliable manner. Accordingly, in case the conductive member 40 is formed by application of solder or the like, the insulating coat layers R on the lateral sides of the transducer elements can be formed up to the top end of the front electrodes by supplying or applying the conductive member 40 to or on the surfaces of the transducer elements which are masked except for electrically connecting portions. However, it is desirable to apply the conductive member 40 in a small thickness because the formation of the acoustic matching layer 32 becomes difficult if the conductive member 40 is largely projected on the upper side. It is not necessarily required to form the conductive member 40 over the entire lengths of joining portions of the transducer elements, and it is rather desirable to leave blank portions void of the conductive member 40 in opposite end portions.

With the ultrasound transducer unit assembly 30 arranged in the manner as described above, the ultrasound transducer 6 is not in an annular form in a strict sense but is in a form similar to an annular array type. The ultrasound transducer 6 therefore makes it possible to apply electronic focus at least at the time of signal transmission or reception. Described below is an electronic focusing mechanism for the ultrasound transducer 30 with reference to FIG. 8.

Figure 8:
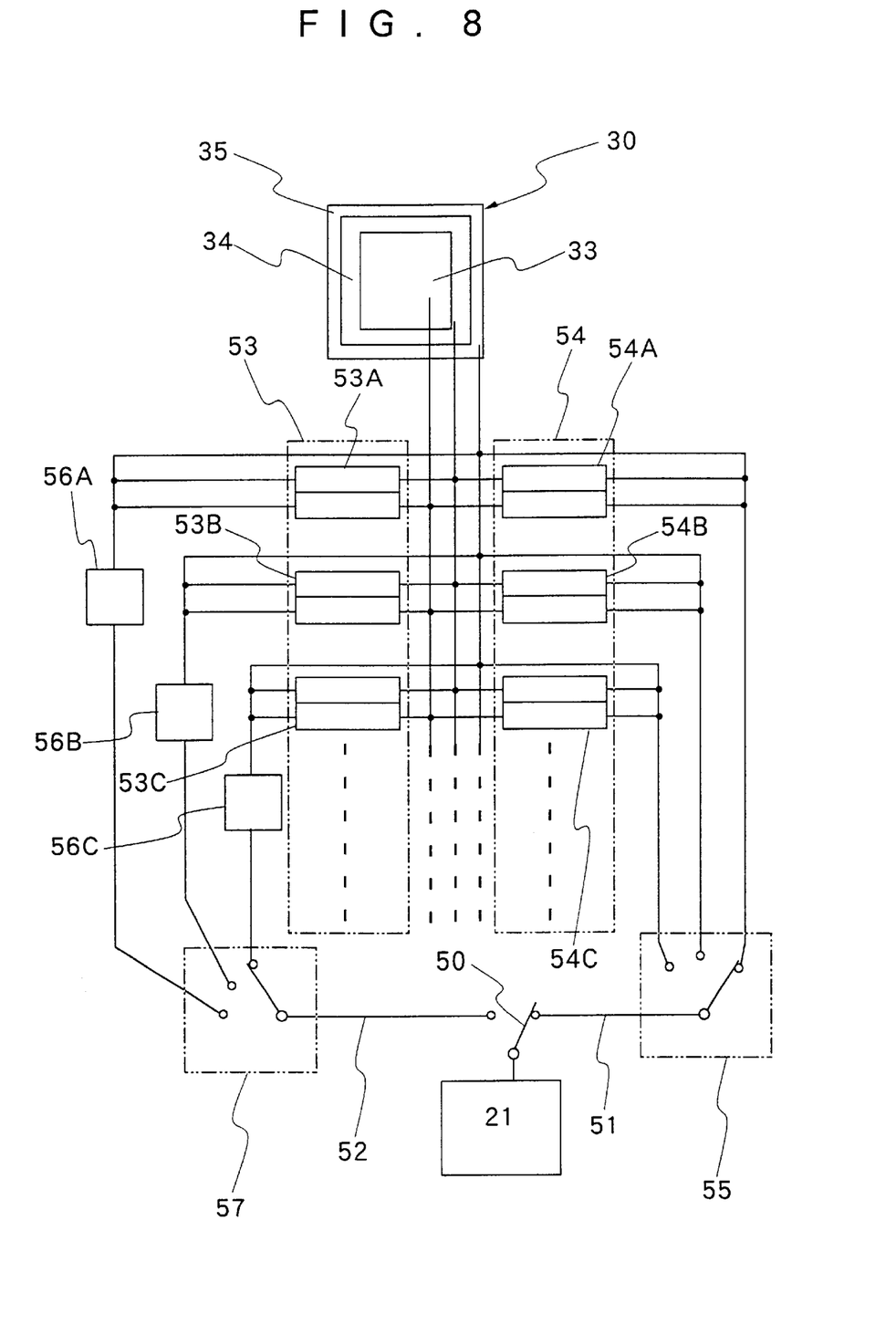
FIG. 8 is a diagram of a circuitry which is adapted to impart an electronic focusing function to the ultrasound transducer.

As shown in FIG. 8, the signal transmission/reception controller 21 is provided with a switch 50 to switch its operation between a transmission mode and a reception mode. In the transmission mode, the signal transmission/reception controller 21 is connected to the transmission side to apply drive signals to the ultrasound transducer 6, and, with a predetermined time delay, switched to the reception mode to receive return echo signals from the transducer 6. The transducer element 33 of the core unit and the transducer elements 34 and 35 of the frame units are driven independently of each other. Transmission signal line 51 and reception signal line 52 are connected to the respective transducer elements 33 to 35 through a delay circuit 53 on the transmission side and a delay circuit 54 on the reception side, respectively.

The delay circuit 53 on the transmission side is arranged to apply no delay time to the transducer elements 35 of the outermost frame unit and to apply a longer delay time to the core transducer element 33 than to the transducer elements 34 of the first frame unit. Therefore, an ultrasound beam which is transmitted from the transducer 6 can be focused to a specific position according to delay characteristics of the delay circuit 53. As a consequence, the ultrasound beam can be focused to a desired position by connecting a plural number of delay circuits 53A, 53B, 53C . . . of predetermined delay characteristics to a switch means 55 as shown in FIG. 8. In this case, dynamic focusing is feasible by sequentially switching the delay circuits during a signal transmission mode.

Similarly, the delay circuit 54 on the reception side is arranged to apply no delay time to the transducer elements 35 of the outermost frame unit and to apply a longer delay time to the core transducer element 33 than to the transducer elements 34 of the first frame unit. Thus, differences in signal reception time of the transducer elements 34 and 35 of the frame units on the outer side of the core transducer element 33 are corrected according to differences in position relative to the core transducer element to bring the reception signals of the respective transducer elements in phase with each other. Further, in a plural number of delay circuits 54A, 54B, 54C . . . of different delay characteristics are connected to a switch means 56 as shown in the drawing, it is possible to move the focus position successively in the fashion of the so-called dynamic focusing by switching the delay circuits successively during a signal reception mode.

Figure 9:
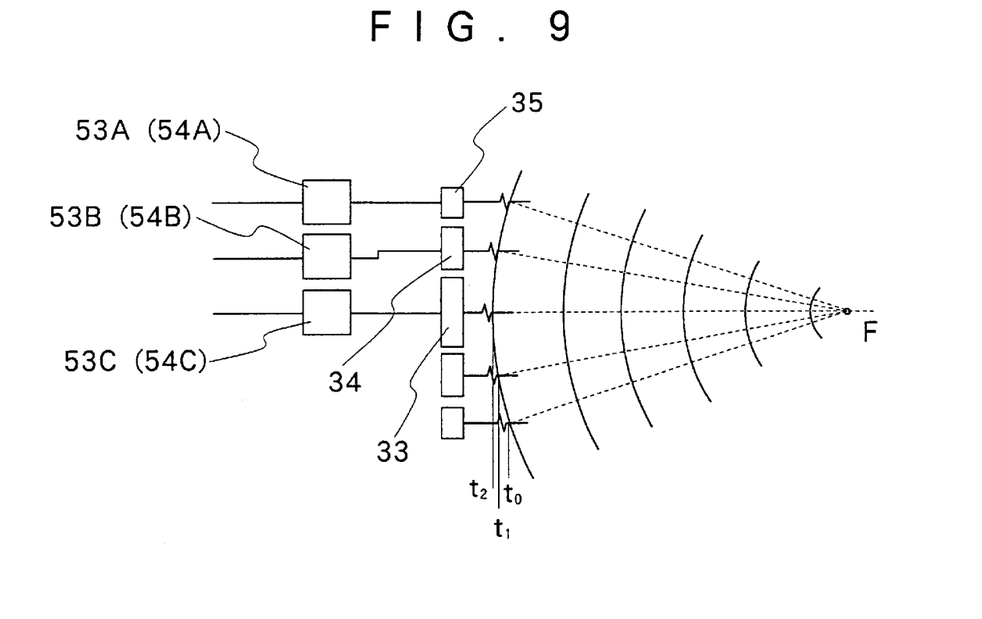
FIG. 9 is a diagrammatic illustration explanatory of an electronic focusing operation by the use of the ultrasound transducer according to the present invention.

The electronic focusing method is diagrammatically shown in FIG. 9. As clear from that figure, an ultrasound beam is transmitted from the transducer elements of the outer second frame unit at a time point $t_0$ without any time delay is applied, and then an ultrasound beam transmitted from the transducer elements 34 of the first frame unit and from the core transducer element 33 after time delays $t_1$, and $t_2$, respectively. As a consequence, the resulting composite ultrasound beam is converged toward one position F at a predetermined depth. This position F is the focal position of electronic focusing. In a similar manner, when in a reception mode, time delays are applied to return echo signals received by the transducer elements 35 of the second frame unit as well as to return signals received by the transducer elements 34 of the first unit and the transducer element 33 of the core unit before summing up the received return echo signals. As a result, the return echo signals from the focal position F, which are received at different positions of the transducer, are matched in phase. Accordingly, the ultrasound transducer 6 can operate with a broad active surface area which corresponds to the sum of active surface areas of all of the transducer elements 33 to 35, free of the problem of phase shifts of received return echo signals across the broad active surface area.

Thus, although the ultrasound transducer is arranged substantially as an annular array type, the transducer elements 33 to 35 which are employed for the core unit and the frame units are all in the form of a straight square rod or block which contains no curved surface on any side thereof. It follows that the transducer elements can be fabricated easily even from an inorganic piezoelectric material such as ceramic semiconductor or the like. Namely, in an ultrasound transducer fabrication process using ceramic semiconductor type transducer elements, which have excellent signal transmission and reception characteristics, the respective transducer elements can be shaped to required forms by simple cutting operations at a lower machining cost and at a higher yield rate since there are less possibilities of cracks or fractures.

Figure 10:
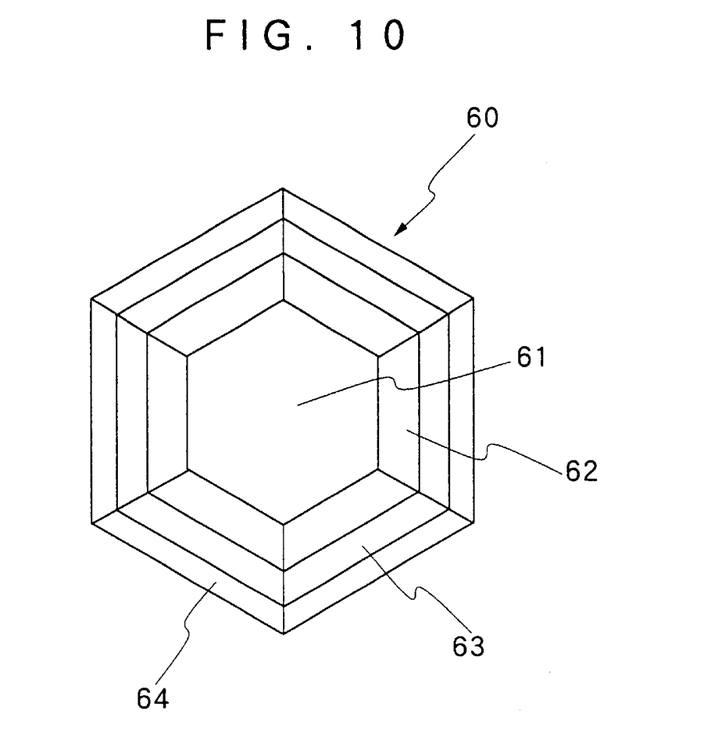
FIG. 10 is a diagrammatic illustration showing a modified arrangement of the transducer elements.

Instead of the square shape as described above, the transducer elements of the respective units of the ultrasound transducer may be arranged in other polygonal shape. For example, the respective units of a transducer element assembly 60 may be arranged in a hexagonal shape as a whole as shown in FIG. 10. In this particular case, a core transducer element 61 of a hexagonal shape is located at the center of the transducer element assembly, and transducer elements 62 to 64 of frame units are arranged in a hexagonal array around the core transducer element 61. The respective transducer elements have substantially the same active surface area. As compared with the above-described square array, this hexagonal array is more closer to the annular array in shape and therefore can be improved further in the electronic focusing function. However, in this case, the assembling work becomes a little complicated because each frame unit is composed of six pieces of transducer elements. Besides, the machining or cutting operation will involve an increased number of steps for obliquely cutting the opposite ends of each transducer element. Nevertheless, required machining operations are still simple in nature since each transducer element has no curved surfaces.

What is claimed is:

1. An ultrasound transducer, comprising:
an array of transducer elements arranged in a polygonal shape on a common plane, said array of transducer elements including a core unit consisting of a single transducer element of the polygonal shape and a plural number of frame units each consisting of a plural number of transducer elements arranged in the polygonal shape around said transducer element of said core unit, each one of said transducer elements of said frame units being formed in the shape of a straight-edged quadrilateral and being electrically connected to adjacent transducer elements of the same frame unit, wherein said core unit and each one of said transducer elements of said frame units are insulated from transducer elements of an adjacent frame unit through coat layer, said insulating coat layers being bonded by means of adhesives to transducer elements in an adjacent frame unit.

2. An ultrasound transducer as defined in claim 1, wherein each one of said transducer elements is formed of a ceramic semiconductor piezoelectric material.

3. An ultrasound transducer as defined in claim 1, wherein said transducer element of said core unit and said transducer elements of said frame units are dimensioned to have substantially the same active surface area.

4. An ultrasound transducer as defined in claim 1, wherein at least two or more frame units are arranged around said transducer element of said core unit.

5. An ultrasound transducer as defined in claim 1, wherein said transducer elements of said core and frame units are arrayed in a square shape as a whole.

6. An ultrasound transducer as defined in claim 1, wherein said transducer elements of said core and frame units are arrayed in a hexagonal shape as a whole.

7. An ultrasound transducer as defined in claim 1, wherein each one of said transducer elements of said core unit and said frame units is provided with a back electrode on the back side and laminated with a front electrode on the front side thereof, said back electrodes of said transducer elements of said core unit and said frame units being placed on a common electrode sheet, and said front electrodes on all of the transducer elements of the same frame unit being electrically connected with each other through bridging conductive members.

8. An ultrasound transducer as defined in claim 7, further comprising a front electrode laminated on the front side of each one of said transducer elements of each frame unit, and insulating coat layers provided on inner and outer sides of each one of said transducer elements, said transducer elements of inner and outer frame units being joined with each other through said insulating coat layers.

9. An ultrasound transducer as defined in claim 7, wherein one of said transducer elements of each frame unit is provided with a notched portion at one corner thereof as a passage for routing a wire from said front electrodes on the front side of said transducer elements to the back side thereof.

10. An ultrasound transducer, comprising:

an array of transducer elements, arranged in a polygonal shape on a common plane, said array of transducer elements including a core unit consisting of a single transducer element of the polygonal shape and a plural number of frame units each consisting of a plural number of transducer elements arranged in the polygonal shape around said transducer element of said core unit, each one of said transducer elements of said frame units being formed in the shape of a straight-edged quadrilateral and being electrically connected to adjacent transducer elements of the same frame unit but insulated from transducer elements of an adjacent frame unit through an insulated coat layer, wherein each one of said transducer elements of said core unit and said frame units is provided with a back electrode on the back side and laminated with a front electrode on the front side thereof, said back electrodes of said transducer elements of said core unit and said frame units being placed on a common electrode sheet, and said front electrodes on all of the transducer elements of the same frame unit being electrically connected with each other through bridging conductive members.

11. An ultrasound transducer as defined in claim 10, further comprising a front electrode laminated on front side of each one of said transducer elements of each frame unit, and insulating coat layers provided on inner and outer sides of each one of said transducer elements, said transducer elements of inner and outer frame units being joined with each other through said insulating coat layers.

12. An ultrasound transducer as defined in claim 10, wherein one of said transducer elements of each frame unit is provided with a notched portion at one corner thereof as a passage for routing a wire from said front electrodes on the front side of said transducer elements to the back side thereof.

* * * * *